United States Patent [19]

Carr et al.

[11] Patent Number: 4,601,843

[45] Date of Patent: Jul. 22, 1986

[54] PHOSPHAZENE BASED FUNCTIONAL FLUID COMPOSITIONS

[75] Inventors: Lawrence J. Carr, Elk Grove Village; George M. Nichols, Evanston; Selwyn H. Rose, Highland Park, all of Ill.

[73] Assignee: Borg-Warner Chemicals, Inc., Parkersburg, W. Va.

[21] Appl. No.: 719,392

[22] Filed: Apr. 2, 1985

[51] Int. Cl.[4] ............... C10M 105/16; C10M 105/70; C10M 105/74
[52] U.S. Cl. ........................... 252/78.5; 252/49.9; 526/193; 526/196; 526/198; 526/206; 526/217; 526/220; 526/222; 526/276; 528/399; 558/80
[58] Field of Search ............... 252/49.9, 78.5; 526/193, 196, 198, 206, 217, 220, 222, 276; 528/399; 260/927 N

[56] References Cited

U.S. PATENT DOCUMENTS

| | | | |
|---|---|---|---|
| B 369,221 | 2/1976 | Kao | 260/927 N |
| 3,291,865 | 12/1966 | Kober et al. | 260/927 N |
| 3,304,350 | 2/1967 | Kober et al. | 260/973 |
| 3,316,330 | 4/1967 | Nichols | 260/927 N |
| 3,370,020 | 2/1968 | Allcock et al. | 260/2 |
| 3,505,087 | 4/1970 | Godfrey | 106/15 |
| 3,545,942 | 12/1970 | Rice et al. | 23/357 |
| 3,990,900 | 11/1976 | Franko-Filipasie et al. | 106/15 FP |
| 4,018,967 | 4/1977 | Roller et al. | 428/425 |
| 4,081,593 | 3/1978 | Lanier et al. | 536/57 |
| 4,110,421 | 8/1978 | Dieck et al. | 423/300 |
| 4,116,891 | 9/1978 | Dieck et al. | 521/89 |
| 4,157,425 | 6/1979 | Dieck et al. | 521/95 |

FOREIGN PATENT DOCUMENTS

1227144  4/1971  United Kingdom ............... 260/968

OTHER PUBLICATIONS

R. A. Shaw et al., "The Phosphazenes (Phosphonitrile Compounds)", Chem. Rev. 62(3), 247, (1962).
Austin et al., "Improved Method for the Synthesis of Poly(Organophosphazenes) and Hindered Cyclophosphazenes", Macromolecules 16(5) 1983, p. 719.
Bornstein et al., "Synthesis and Melting Behavior of Certain (Aryloxy) Cyclotriphosphazene Polymer", Inorg. Chem. 1985, 24, 625–628.
Dehmlow et al., *Phase Transfer Catalysis*, Verlag Chimie, 1980, p. 77.
Singler et al., "Synthesis and Evaluation of Phosphazene Fire Resistant Fluids", Army Science Conference Paper A117298, 1982.
Fluoroalkylphosphonitrilates: A New Class of Potential Fire-Resistant Hydraulic Fluids and Lubricants. I., E. Kober et al., Asle Transactions 7 (1964), pp. 389–397.
Fluoroalkyl Phosphonitrilates, a New Class of Potential Fire-Resistant Hydraulic Fluids and Lubricants, H. Lederle et al., Journal of Chemical and Engineering Data, vol. 11, No. 2 (Apr. 1966), pp. 221–228.

*Primary Examiner*—Paul Lieberman
*Assistant Examiner*—Robert A. Wax
*Attorney, Agent, or Firm*—Emily A. Richeson

[57] ABSTRACT

A functional fluid composition is provided which comprises a plurality of different phosphazene compounds of the general formula $(P=N)_n (R)_a (R')_b (R'')_c (R''')_d$ wherein R is at least one alkoxy moiety described by the general formula $-OCH_2(CF_2)_y X$, with X being hydrogen or fluorine and y being equal to 1 to about 10; R', R" and R''' are different aryloxy moieties, each of R', R" and R''' being selected from the group consisting of phenoxy, alkoxy phenoxys, alkyl phenoxys, chlorinated phenoxys, fluorinated phenoxys, aryl phenoxys, phenoxy phenoxys, fluoroalkyl phenoxys, fluoroalkoxy phenoxys, chlorinated phenoxy phenoxys, fluorinated phenoxy phenoxys and mixtures thereof; n is equal to 3 to about 4 for each of said phosphazene compounds, each of a, b, c and d is equal to or greater than zero such that the sum $a+b+c+d$ is equal to $2n$; and for the composition as a whole, the average value of each of a, b, c and d is greater than 0.

18 Claims, No Drawings

4,601,843

PHOSPHAZENE BASED FUNCTIONAL FLUID COMPOSITIONS

BACKGROUND OF THE INVENTION

This invention relates to novel cyclic phosphazenes and phosphazene based functional fluid compositions.

A variety of phosphazene compositions and methods of preparation are known in the art. U.S. Pat. No. 3,291,865 to Kober, et al discloses non-flammable, hydrolytically stable phosphazene compositions for use as hydraulic fluids, lubricants and additives. These phosphazenes are substituted by an aryloxy and a polyfluoroalkoxy substituent, and are synthesized by forming the alkali metal salt of the fluorinated alkanol followed by reaction of the salt and a salt of a phenol with a phosphonitrilic chloride.

The alkoxy substituent may be any $C_2$ to $C_{21}$ polyfluoroalkoxy substituent. Examples of polyfluoro alcohols useful in providing this substituent include 1,1,3-tri-H-tetrafluoropropyl alcohol, 1,1,5-tri-H-octofluoropentyl alcohol, 1,1,7-tri-H-dodecafluoroheptyl alcohol, 1,1-di-H-trifluoroethyl alcohol, 1,1-di-H-heptaflurobutyl alcohol, 1,1-di-H-pentadecafluorooctyl alcohol and mixtures thereof. The aryloxy substituent may be derived from any of a variety of phenolic compounds, including monohydroxy phenols such as phenol and naphthol, phenoxyphenols, alkoxy-substituted phenols, alkyl-substituted phenols, aryl-substituted phenols, halogen-substituted phenols, halogen-alkyl-substituted phenols, and halogen-alkoxy-substituted phenols. Only phosphazene based compositions with one type of aryloxy substituent are exemplified. Similar phosphazene based compositions are described in the articles "Fluoroalkyl Phosphonitrilates: A New Class of Potential Fire-Resistant Hydraulic Fluids and Lubricants", H. Lederle, E. Kober and G. Ottmann, Journal of Chemical and Engineering Data, Volume 11, No. 2, April 1966; and "Fluoroalkyl Phosphonitrilates: A New Class of Potential Fire-Resistant Hydraulic Fluids and Lubricants", E. Kober, H. Lederle and G. Ottmann, ASLE Transactions 7, 389–397 (1964).

Polyfluoroalkoxy-substituted phosphazenes are disclosed in U.S. Pat. No. 3,304,350 to Kober, et al. Examples of useful polyfluoro alcohols include 1,1-di-H-trifluoroethyl alcohol, 1,1-di-H-pentafluoropropyl alcohol, 1,1-di-H-heptafluorobutyl alcohol, 1,1-di-H-pentadecafluorooctyl alcohol, 1,1,3-tri-H-tetrafluoropropyl alcohol and 1,1,5-tri-H-octafluoropentyl alcohol. A variety of other phosphazene compositions are known in the art. U.S. Pat. No. 3,370,020 to Allcock, et al, U.S. Pat. No. 3,505,087 to Godfrey, U.S. Pat. No. 4,081,593 to Lanier, U.S. Pat. No. 4,018,967 to Roller, et al, U.S. Pat. Nos. 4,110,421, 4,157,425 and 4,116,891 to Dieck, et al, U.S. published patent application No. B 369,221 to Kao, U.S. Pat. No. 3,990,900 to Franko Filipasic, et al and U.S. Pat. No. 3,545,942 to Rice, et al disclose phosphazenes which may be substituted by a variety of alkoxy, alkenyloxy, arylalkoxy or aryloxy groups.

However, many known phosphazene based compositions, such as those discussed above, have limitations which make them unsuitable for many functional fluid applications.

A functional fluid composition usually must demonstrate acceptable characteristics with regard to at least three properties; (1) fire resistance, (2) low temperature fluidity, and (3) compatibility with seal compositions. Failure of a functional fluid with respect to any of these properties may have serious consequences under the conditions of use.

In 1953 and 1954 the U.S. aircraft carriers "Leyte" and "Bennington", respectively, were heavily damaged due in part to explosions caused by flammable hydraulic fluids. Consequently, fire resistance is a critical characteristic for military, industrial or consumer applications. Unfortunately, adequate fire resistance is lacking for many phosphazene based compositions, particularly those wherein the functional groups are moieties which include unhalogenated, relatively large alkyl substituents.

However, phosphazene based compositions which exhibit good flame retardancy may also be solids under most conditions of use. This may make them unsuitable for certain applications, such as hydraulic fluids and lubricants, wherein liquidity may be required. Even if a phosphazene composition initially is a homogenous liquid, many phosphazene based compositions tend to completely or partially solidify or to separate into different phases after standing for a period of time. This tendency is particularly problematic for low temperature applications, such as outdoor hydraulic systems, wherein the functional fluid may be exposed to very low temperatures for prolonged periods of time. Such a tendency to solidify or undergo phase separation may make a composition unsuitable for certain uses, such as functional fluids in sealed hydraulic systems, wherein monitoring of the state of the phosphazene is impossible and replacement is impracticable.

Although certain phosphazene based compositions may remain liquid for a relatively long period of time, this liquidity may be due to impurities present in the composition, rather than to the characteristics of the composition per se. These impurities may cause degradation of the phosphazene compounds over a period of time or may corrode the apparatus with which the composition comes in contact, thereby contributing to failure of the system in which the composition is used.

Although certain phosphazene based fluids, such as those wherein the phosphazenes are functionalized by fluorinated phenoxy and/or fluorinated alkoxy moieties, may exhibit acceptable fire resistance, these compositions may be incompatible with elastomers and other materials used to form seals in hydraulic and other functional systems. Such incompatability may cause the seals to swell or shrink excessively, thereby causing system failure.

Price and supply are also considerations. Although a variety of alkoxy and aryloxy compounds may be used to form cyclophosphazene ester compositions, these compounds vary widely in cost and availability. It is therefore advantageous to be able to use relatively low cost and readily obtainable materials to synthesize a phosphazene based functional fluid composition having good fire resistance, low temperature fluidity and elastomer compatibility.

SUMMARY OF THE INVENTION

The present invention is a functional fluid composition comprising a plurality of different phosphazene compounds of the general formula: $(P=N)_n (R)_a (R')_b (R'')_c (R''')_d$ wherein R is at least one alkoxy moiety described by the general formula: $-OCH_2(CF_2)_yX$, with X being hydrogen or fluorine and y being equal to 1 to about 10; R', R'' and R''' are different aryloxy moieties, each of R', R'' and R''' being selected from the group consisting of phenoxy, alkoxy phenoxys, alkyl phenoxys, chlorinated phenoxys, fluorinated phenoxys, aryl phenoxys, phenoxy phenoxys, fluoroalkyl phenoxys, fluoroalkoxy phenoxys, chlorinated phenoxy phenoxys, fluorinated phenoxy phenoxys, and mixtures thereof; n is equal to 3 to about 4; for each of said phosphazene compounds, each of a, b, c and d is equal to or greater than 0 such that the sum a+b+c+d is equal to 2n, and; for the composition as a whole, the average value of each of a, b, c and d is greater than zero.

The present invention also includes the product obtained by the process comprising reacting a dichlorophosphazene compound, having 3 to about 4 phosphazene units, with (a) at least one alkanol reactant generally described by the formula: $HOCH_2(CF_2)_yX$, with X being hydrogen or fluorine and y being equal to 1 to about 10, and (b) at least three different phenolic reactants selected from the group consisting of phenol, alkoxy phenols, alkyl phenols, chlorinated phenols, fluorinated phenols, aryl phenols, phenoxy phenols, fluoroalkyl phenols, fluoroalkoxy phenols, chlorinated phenoxy phenols, fluorinated phenoxy phenols, and mixtures thereof, said reaction occurring in a medium comprising a mixture of water, a base, a water-immiscible solvent and a phase-transfer catalyst.

DETAILED DESCRIPTION OF THE INVENTION

The present invention is a functional fluid composition comprising a plurality of different phosphazene compounds of the general formula: $(P=N)_n (R)_a (R')_b (R'')_c (R''')_d$. Each of these compounds includes a cyclic substrate of 3 to about 4 phosphazene units [—P=N—]. The substituents R, R', R" and R''' are all organic moieties esterified to the phosphazene substrate, i.e. bonded to phosphorus through oxygen. The phosphazene may be a pentameric, tetrameric or trimeric cyclic compound. However, cyclic trimeric and tetrameric phosphazenes, wherein n is 3 or 4, are preferred. Mixtures of trimeric and tetrameric phosphazenes may also be used; however, a predominance of cyclic trimeric phosphazenes is most preferred.

According to the present invention, in each of the phosphazene compounds R is at least one alkoxy moiety which may be described by the general formula: $—OCH_2—(CF_2)_yX$. In this formula X may be hydrogen or fluorine, such as in 2,2-difluoroethoxy or 2,2,2-trifluoroethoxy, respectively. Fluorine is preferred. Further, y may be equal to an integer from 1 to about 10, such as in fluorinated ethoxy, propoxy, butoxy, pentoxy, heptoxy, nonoxy and undecoxy moieties. This fluorinated alkoxy moiety is usually derived from the corresponding fluorinated alkanol, e.g. ethoxy from ethanol, propoxy from propanol, etc. Examples of suitable alkanols include 1,1,9-tri-H-hexadecafluoronoyl alcohol; 1,1,11-tri-H-eicosafluoroundecyl alcohol; 1,1-di-H-pentadecafluorooctyl alcohol; 1,1-di-H-pentafluoropropyl alcohol; 1,1,7-tri-H-dodecafluoroheptyl alcohol; 1,1,2-tri-H-difluoroethyl alcohol (2,2-difluoroethanol); and 1,1-di-H-trifluoroethyl alcohol (2,2,2-trifluoroethanol). Preferably, however, y is equal to 1 to about 3, such as in ethyl, propyl and butyl fluorinated alcohols, as a substantial proportion of longer alkoxy moieties may lead to a significant increase in viscosity. Trifluoroethanol is most preferred.

Although preparation of the phosphazene composition may be simplified by the halogenated alkoxy moiety being homogenous, a mixture of different halogenated alkoxy moieties, consistent with the above formula, may be included, such as mixtures of 2,2-difluoroethoxy and 2,2,3,3,3-pentafluoropropoxy. When a mixture of different fluorinated alkoxy moieties is included, it is preferred that at least 75% by weight of the alkoxy moieties, based upon the combined weight of all of the alkoxy moieties present in all of the phosphazene compounds that together make up the functional fluid composition, be trifluoroethoxy. More preferably, this amount should be at least 90% by weight.

The phosphazene composition also includes at least three different aryloxy groups, represented by R', R" and R''' in the formula above, which are esterified to phosphazene compounds in the composition. These aryloxy groups differ from each other by at least one of (i) the presence or absence of substitution to the aryl ring, (ii) the position of substitution on the aryl ring, (iii) the identity of the substituent(s), and (iv) the number of substituents. Thus, aryloxy groups which are isomers of each other are considered to be distinct for the purposes of the present invention.

Consistent with this distinction between isomers, the aryloxy substituents R', R" and R''' are selected from the group consisting of phenoxy, alkoxy phenoxys such as m-methoxyphenoxy, m,p-dimethoxyphenoxy, p-methoxyphenoxy, m-ethoxyphenoxy and p-propoxyphenoxy as well as other mono, di and trialkoxy phenoxys; alkyl phenoxys such as m-propylphenoxy, p-tert-butylphenoxy, 3,5-dimethylphenoxy, 2,4-dimethylphenoxy, 2,3-dimethylphenoxy, 2,4,6-tri-methylphenoxy, 3,4-dimethylphenoxy, p-ethylphenoxy, m-ethylphenoxy, m-isobutylphenoxy, o-ethylphenoxy, p-methylphenoxy and m-methylphenoxy as well as other mono, di and trialkyl phenoxys; mono, di, tri, tetra and penta chlorinated or fluorinated phenoxys such as p-chlorophenoxy, m-chlorophenoxy, 3,5-dichlorophenoxy, 2,4,6-trichlorophenoxy, 2,3,4,5-tetrachlorophenoxy, pentafluorophenoxy and p-fluorophenoxy; aryl phenoxys such as p-phenylphenoxy, m-phenylphenoxy and (methylphenyl)phenoxys; phenoxy phenoxys such as p-phenoxyphenoxy; mono, di and trifluoroalkyl phenoxys such as p-(difluoromethyl)phenoxy, m-(trifluoromethyl)phenoxy, and m,p-di(trifluoromethyl)phenoxy; mono, di and tri-fluoroalkoxy phenoxys such as p-(difluoromethoxy)phenoxys and m-(2,2,2-trifluoroethoxy)phenoxys; mono, di, tri, tetra and pentachlorinated or fluorinated phenoxy phenoxys such as 4-(3,4-difluorophenoxy)phenoxy and 4-(3,4-dichlorophenoxy)phenoxy.

Preferably, at least 80% by weight of R', R" and R''', based on the combined weight of R', R" and R''' for all of the phosphazene compounds taken together, are selected from the group consisting of phenoxy, alkyl phenoxys, alkoxy phenoxys, and mixtures thereof. As fire resistance is generally inversely related to the length of alkyl groups present in the aryloxy moiety, it is more preferred that at least 90% by weight of the aryloxy moieties be selected from the group consisting of phenoxy, methylphenoxys, ethylphenoxys, dimethylphenoxys and mixtures thereof. It is more preferred that at least 80% by weight of the aryloxy moieties be phenoxy, m-methylphenoxy and p-methylphenoxy. Amounts of at least 90% by weight phenoxy, m-methylphenoxy and p-methylphenoxy are most preferred.

Any of R', R" and R''' may also be selected from mixtures of the above aryloxy substituents, such as when R' is phenoxy, R" is a mixture of m-methylphenoxy and p-methylphenoxy, and R''' is p-ethylphenoxy. Thus the invention also includes the embodiment wherein the functional fluid composition comprises as many as four, five, six or more of the above aryloxy groups esterified to phosphazene compounds.

The phosphazene compounds of the functional fluid composition may be synthesized by the esterification of dichlorophosphazenes. However, incomplete substitution may result in the presence of residual chloride in the phosphazene compound, thereby making the compound susceptible to hydrolytic degradation. Although the functional fluid of the present invention may contain small quantities, on the order of a few tenths of a percent by weight, of incompletely substituted phosphazenes without suffering from deleterious effects, the present invention is directed to phosphazene compounds which are fully substituted, e.g. wherein the sum of the number of aryloxy and fluorinated alkoxy substituents, $a+b+c+d$, is equal to $2n$.

As long as the sum $a+b+c+d$ for each phosphazene compound is equal to $2n$, the individual value of each of a, b, c and d may be greater than or equal to zero. Thus, the functional fluid composition may contain one or more phosphazene compounds which are substituted by only one, two or three of R, R', R" and R'''.

For the functional fluid composition as a whole, an average value may be defined for each of the subscripts a, b, c and d. This average value is the sum of each subscript for the phosphazene compounds in the functional fluid composition, divided by the total number of different phosphazene compounds in the composition consistent with the above formula. For example, for a functional fluid composition comprising three different phosphazene compounds $(P=N)_3R_2R'_1R'''_3$, $(P=N)_3R'_4R''_2$, and $(P=N)_3R_2R'_1R''_2R'''_1$, the average value of a is $(2+2)/3$ or approximately 1.3, the average value of b is $(1+4+1)/3$ or 2, the average value of c is $(2+2)/3$ or approximately 1.3, and the average value of d is $(3+1)/3$ or approximately 1.3. While the individual value of a, b, c and d in each phosphazene compound may be greater than or equal to zero, for the functional fluid composition as a whole, the average value of each of these subscripts must be greater than zero, e.g. each of R, R', R" and R''' must be present in at least one phosphazene compound of the functional fluid composition.

It should further be noted that the present invention is also directed to a novel phosphazene composition of the general formula $(P=N)_n(R)_a(R')_b(R'')_c(R''')_d$, with R, R', R" and R''' as discussed above, wherein each of a, b, c and d is greater than zero, i.e. at least one fluorinated alkoxy substituent and at least three different aryloxy substituents are present in the same phosphazene compound.

Although the ratio of alkoxy to aryloxy substituents may vary substantially from phosphazene compound to phosphazene compound, an alkoxy:aryloxy ratio may be defined based on the number of alkoxy and aryloxy substituent groups present in the functional fluid composition as a whole. In the preferred embodiment, the ratio of the average number of halogenated alkoxy groups to aryloxy groups, e.g. the ratio of the average value of a to the sum of the average values of b, c and d, is about 0.5:1 to about 8:1. More preferably, this ratio is about 0.8:1 to about 5:1. Ratios of about 1.3:1 to about 1.9:1 are most preferred.

Preferably, each of the phosphazene compositions in the functional fluid is present in an amount which constitutes less than 70% by weight of the total phosphazene content of the composition, as a more even distribution of phosphazene compounds has been observed to assist in maintaining prolonged fluidity at low temperatures. For example, two phosphazene compounds may be present in ratios by weight of 31:69, 65:35, 50:50, or 57:43. However, an increased tendency toward low temperature fluidity has been observed when more than two different phosphazene compounds are present in the composition. Consistent with this observation, although the functional fluid may comprise two or more different phosphazene compounds, in the preferred embodiment the functional fluid composition includes at least three different phosphazene compounds. Although these compounds may be present in various amounts, it is preferred that each compound constitute less than 50% by weight of the total phosphazene content of the composition. For example, in a functional fluid containing three different phosphazene compounds these compounds may be present in ratios by weight of 36:48:16 or 8:49:43. More preferably, however, at least two of the phosphazene compounds each constitute less than 35% by weight of the total phosphazene content of the composition, such as in distributions of 34:48:18, 34:32:34, 28:24:48, etc.

The phosphazene compounds useful in the present invention may be synthesized using processes known in the art, such as the alkali metal salt method of U.S. Pat. No. 3,291,865 to Kober, et al or U.S. Pat. No. 3,370,020 to Allcock, et al, or the phase transfer method of U.S. Appln. Ser. No. 560,096 filed Dec. 12, 1983, the disclosure of which is herein incorporated by reference. Example 9 demonstrates preparation of one embodiment of the functional fluid composition of the present invention by using the alkali metal salt method. However, the phase transfer method of synthesis is preferred as this method yields a variety of different phosphazene compounds, wherein the aryloxy and alkoxy substituents are present in different proportions, using a relatively simple and cost effective procedure. The bulk phase transfer method, wherein the dichlorophosphazene substrate is contacted with the phenolic reactants and the fluorinated alkanol reactant at the same time, is particularly preferred as this method tends to yield a broader, more evenly distributed product mix.

Consequently, the preferred embodiment of the present invention may be described as the product of the process comprising reacting a dichlorophosphazene compound with (a) at least one alkanol reactant described by the general formula: $HOCH_2(CF_2)_yX$, where X is hydrogen or fluorine and y is equal to 1 to about 10, and (b) at least three different phenolic reactants selected from the group consisting of phenol, alkoxy phenols, alkyl phenols, chlorinated phenols, fluorinated phenols, aryl phenols, phenoxy phenols, fluoroalkyl phenols, fluoroalkoxy phenols, chlorinated phenoxy phenols, fluorinated phenoxy phenols and mixtures thereof, said reaction occurring in a medium comprising a mixture of water, a base, a water-immiscible solvent and a phase-transfer catalyst. The fluorinated alkanol reactant and the phenolic reactants correspond, of course, to the fluorinated alkoxy and the aryloxy moieties discussed above.

The phase transfer catalyst preferably is an alkyl, aryl or aralkyl ammonium or phosphonium salt. More preferably, as disclosed in U.S. Appln Ser. No. 560,096, incorporated herein by reference, the phase-transfer catalyst is one having the structure $(R^{iv})_4AX$, with the $(R^{iv})$'s being the same or different alkyl, aryl or aralkyl group, A being nitrogen or phosphorus, and X being halogen, OH, HSO$_4$, NO$_3$, BH$_4$, IO$_4$, ClO$_4$, CN, N$_3$, OCH$_3$, tosylate or benzoate. Most preferably, the (R$^{iv}$)'s are the same or different alkyl group, and X is chlorine or bromine.

In order to minimize the presence of any residual phosphazene-bound chlorine in the product, and to encourage complete substitution, it is preferred that the molar ratio of alkanol reactant and phenolic reactants, combined, to phosphazene units be at least 2:1. Consequently, when the dichlorophosphazene compound is a trimeric phosphazene, the molar ratio of the combination of alkanol reactant and phenolic reactants to the dichlorophosphazene compound should be at least 6:1. Although a molar excess of alkanol and phenolic reactants may be present in the reaction mixture, this excess preferably is minimized due to cost considerations. As a result, preferred molar ratios of alkanol and phenolic reactants combined to phosphazene units are about 2.5:1 or less.

It is preferred that the molar ratio of alkanol reactant to phenolic reactants be about 5:1 to about 0.8:1, with ratios of about 4:3 to about 2:1 being most preferred. Due to the relatively low cost of phenol in relation to the cost of other phenolic feedstocks, it is further preferred that about 40% to about 60% by weight of the phenolic reactants be phenol.

SPECIFIC EMBODIMENTS

In the presentation of specific embodiments below, the term "PTC bulk" indicates that a particular composition was synthesized by a catalyzed phase transfer process wherein the dichlorophosphazene feedstock is reacted with all of the substituent reagents at the same time, similar to the procedures described for Example 1 and Comparative Example C13, with post-reaction of the initial product with appropriate alkali metal aryloxy and/or fluorinated alkoxy salts to drive the reaction to completion.

The term "PTC sequential" indicates that a particular composition was synthesized by means of a phase transfer process, similar to that described in Comparative Example C18, wherein the aryloxy reagents are allowed to react with the dichlorophosphazene feedstock for a period of time before contact with the fluorinated alkoxy reagent. Similarly, "Na salt, sequential" indicates a process according to the alkali metal salt method, similar to that described for Example 9, wherein the aryloxy reagents are allowed to react with the dichlorophosphazene feedstock for a period of time before addition of the fluorinated alkoxy reagent.

In Table I, and for the subsequent Examples, viscosity was measured according to ASTM D-445; Pour Point was measured according to ASTM D-97; Acid Number relates to Fed. Test Method 5105.3 Fed-Std-791a; Flash Point was measured by ASTM D-92 (micro-cup method); "AIT" refers to "autogenous ignition temperature", i.e. the temperature at which the composition spontaneously ignites at a specific pressure, according to ASTM G-72; The "Emulsion Test" reported in Table I refers to ASTM Standard D1401; "Foaming Tendency" refers to ASTM Standard D892; "Elastomer Compatibility" refers to Federal Test Method 3603, Fed-Std-791; and "Hydrolytic Stability" and CFR Compression Ratio refer to Military Specification Mil-H-19457C(SH), Par. 4.5.2.

Example 1 exemplifies the preparation of the product of the present invention by a PTC bulk process, with post reaction with potassium phenoxide.

EXAMPLE 1

An aqueous solution containing 217.2 g, of 2,2,2-trifluoroethanol, 63.5 g phenol, 73.0 g of a mixture of m-methylphenol and p-methylphenol, 223.5 g KOH pellets and 365 mL of water is added drop-wise to a solution containing 200 g of purified hexachlorocyclotriphosphazene containing 2% or less of octachlorocyclotetra phosphazene, 67 g of tetrabutyl ammonium bromide and 888 mL of chlorobenzene to form an organic phase and an aqueous phase. The organic phase was stirred and maintained at 25°–30° C. during the addition period. After addition of the aqueous solution, the organic phase was heated at 40° C. for approximately 4–5 hours, followed by separation of the organic phase and aqueous phase and the extraction of the organic phase with dilute H$_2$SO$_4$ to remove the tetrabutyl ammonium halide catalyst. Potassium phenoxide (26 g) was added to the organic phase and the resulting solution refluxed for 5 hours. The organic phase was then washed sequentially with a dilute base and a dilute acid, after which the organic phase was passed through a bed of activated alumina to remove residual catalyst. After removal of the chlorobenzene solvent by evaporation under reduced pressure there remained 303 g of a clear, colorless oil. This oil was analyzed as containing about 0.15% by weight residual chlorine and as consituting an essentially pure mixture of phosphazene compounds of the average composition:

$$P_3N_3(OCH_2CF_3)_{3.6}(OC_6H_5)_{1.2}(OC_6H_4CH_3)_{1.2}$$

This average composition was confirmed by elemental analysis, gas chromatography and proton magnetic resonance.

The physical properties of this composition are reported below in Table I. The distribution of phosphazene compounds in this composition, as indicated by gas chromatographic analysis, are reported below in Table II. These structures were confirmed by high resolution mass spectroscopy.

TABLE I

| Physical Properties of Composition of Example 1 | |
|---|---|
| Viscosity | |
| 40° C.: | 51.9 cPs |
| 100° C.: | 6.2 cPs |
| Pour Point: | −24° C. |
| Acid Number: | 0.01 |
| Density: | 1.45 g/mL |
| Flash Point: | >288° C. |
| CFR Compression Ratio: | 46:1 |
| High Pressure AIT: | 282° C. |
| Emulsion Test: | Pass |
| Hydrolytic Stability: | Pass |
| Foaming Tendency: | Pass |
| Elastomer Compatibility (% Volume Change) | |
| EPR: | −1.65% |
| Viton I: | +8.76% |
| Viton II: | +6.55% |

TABLE II

Components of Composition of Example 1

| Component | Distribution (wt %) |
|---|---|
| $P_3N_3(OCH_2CF_3)_6$ | 2.3 |
| $P_3N_3(OCH_2CF_3)_5(OAr)$ | 20.8 |
| $P_3N_3(OCH_2CF_3)_4(OAr)_2$ | 42.1 |
| $P_3N_3(OCH_2CF_3)_3(OAr)_3$ | 25.6 |
| $P_3N_3(OCH_2CF_3)_2(OAr)_4$ | 6.8 |
| $P_3N_3(OCH_3CF_3)(OAr)_5$ | 2.4 |
| $P_3N_3(OAr)_6$ | Trace |

In reporting the composition of the components in Table II and in subsequent tables, the aryloxy components, e.g., for Example 1, phenoxy, m-methylphenoxy and p-methylphenoxy, are combined together and reported as the number of aryloxy components, "OAr". Samples of the composition of Example 1 were stored for one year at −20° C. During this time these samples remained liquid, with no evidence of crystallization or phase separation.

EXAMPLE 2

The proportions and procedure of Example 1 were scaled up to yield approximately 30 gal. of an essentially pure mixture of phosphazene compounds. As indicated by the physical properties reported below in Table III, this composition exhibited physical properties similar to those reported for the composition of Example 1, with the composition of Example 2 showing an improved CFR Compression Ratio of 50:1.

TABLE III

Physical Properties of Composition of Example 2

| Viscosity | |
|---|---|
| 40° C.: | 50.8 cPs |
| 100° C.: | 6.1 cPs |
| Pour Point: | −21° C. |
| Acid Number: | 0.02 |
| Flash Point: | >288° C. |
| CFR Compression Ratio: | 50:1 |
| High Pressure AIT: | 288° C. |
| Hydrolytic Stability: | Pass |
| Foaming Tendency: | No Foam |

EXAMPLES 3–5

Compositions containing various ratios of trifluoroethoxy groups to phenoxy, m-methylphenoxy and p-methylphenoxy were prepared from 2,2,2-trifluoroethanol, phenol and a mixture of m-methylphenol and p-methylphenol, according to the procedure outlined above for Example 1. By adjusting the proportion of trifluoroethanol to aryloxy compounds, various ratios of trifluoroethoxy (TFE) to aryloxy (ArO) groups may be obtained in the phosphazene product. The ratios of these groups in the product and the corresponding viscosities are pour points are indicated below in Table IV.

TABLE IV

Effect of Stoichiometry on Composition Viscosity and Pour Point

| Ex # | Average # of Moles | | | Visc. 40° C. (cPs) | Pour Point °C. |
|---|---|---|---|---|---|
| | (—P=N—)$_3$ | TFE | ArO | | |
| 3 | 1.0 | 3.6 | 2.4 | 56.3 | −19 |
| 4 | 1.0 | 3.7 | 2.3 | 52.6 | −22 |
| 5 | 1.0 | 3.9 | 2.1 | 45.7 | −24 |

Another embodiment of the invention, containing a mixture of trifluoroethoxy, phenoxy, m-methylphenoxy and p-methylphenoxy substituents and prepared by a PTC bulk process with post-reaction with potassium phenoxide, is exemplified in Example 6.

EXAMPLE 6

An aqueous solution containing 984 g 2,2,2-trifluoroethanol, 354 g phenol, 407 g of a mixture of m-methylphenol and p-methylphenol, 1138 g KOH pellets and 1835 mL water was added drop-wise to a solution containing 1005 g of purified hexachlorocyclotriphosphazene (98% trimer, 2% tetramer), 333.5 g of tetrabutyl ammonium bromide and 4000 mL of chlorobenzene to form an organic phase and an inorganic phase. The organic phase was stirred and maintained at 25°–30° C. during the addition period, then heated to 40° C. for four hours. The organic phase was separated and extracted with 5% aqueous HCl to remove the catalyst. Potassium phenoxide (138 g) was added to the organic phase, and the solution refluxed for five hours. The organic phase was sequentially washed with a dilute base and a dilute acid. The solvent was removed by evaporation under reduced pressure, 90 g of anhydrous calcium carbonate was added to the residue and the mixture vacuum distilled. This resulted in 1089 g of liquid distillate which had a pour point of −23° C., a viscosity at 40° C. of 51.3 cPs and an acid number of 0.1. A sample of this distillate had not begun to crystallize or undergo phase separation after storage for one year at −24° C.

COMPARATIVE EXAMPLE C7

The PTC bulk procedure of Example 6 was repeated, except that pure m-methylphenol was substituted for the mixture of m-methylphenol and p-methylphenol used in Example 6. This resulted in a fluid product which was completely crystallized after storage at −24° C. for several days.

Example 8 exemplifies the preparation of a functional fluid composition of the present invention using a tetrameric phosphazene feedstock.

EXAMPLE 8

An aqueous solution containing 67.32 g of trifluoroethanol, 24.26 g of a mixture of m-methylphenol and p-methylphenol, 21.12 g of phenol, 72.09 g KOH pellets and 107 mL of water was added gradually to a solution containing 63.74 g of purified octachlorocyclotetraphosphazene, 21.28 g tetrabutyl ammonium bromide and 290 mL of chlorobenzene. The resulting mixture was reacted according to the conditions and procedures described above in Example 6, except that the crude product was purified by the additional step of contacting it with activated alumina. This resulted in 125 g of product which was a colorless oil. This product had a viscosity at 40° C. of 98.0 cPs and a pour point of −26° C. A viscosity and pour point of a fluid made of purified hexachlorocyclotriphazene, using the same stoichiometry, had a viscosity at 40° C. of 56.3 cPs and a pour point of −21° C.

Example 9 exemplifies preparation of an embodiment of the present invention by the alkali metal salt, sequential addition method.

EXAMPLE 9

Sodium metal (34.5 g) was gradually added to a solution containing 103.5 g phenol, 1,000 mL of tetrahydrofuran and 67.2 g of a tar acid mixture of the following composition wherein "TM Phenol" indicates trimethylphenol and "$C_3$ Phenols" indicates propylphenols:

| Component | Wt. % |
|---|---|
| Phenol | .1 |
| o-Methylphenol | Trace |
| p-Methylphenol | Trace |
| m-Methylphenol | .1 |
| o-Ethylphenol | Trace |
| 2,4-Xylenol | 1.1 |
| 2,5-Xylenol | 1.1 |
| 2,4,6-TM Phenol | .7 |
| 2,3-Xylenol | 9.9 |
| p-Ethylphenol | 15.2 |
| m-Ethylphenol | 38.3 |
| 3,5-Xylenol | 20.2 |
| 3,4-Xylenol | 7.2 |
| $C_3$ Phenols | 6.1 |
| Total | 100.0% |

The resulting mixture was refluxed for 15 hours. A solution of sodium trifluoroethoxide was prepared in a similar manner by adding 37.95 g of sodium metal to 172.5 g of 2,2,2-trifluoroethanol and 1,000 mL of tetrahydrofuran (THF). The solution of sodium aryloxides in tetrahydrofuran was added drop-wise to a solution containing 174 g of purified hexachlorocyclotriphosphazene in one liter of THF and the resulting mixture heated at 60°-65° C. for five hours. The mixture was cooled to room temperature, and the solution of sodium trifluoroethoxide added in a drop-wise manner. This resulted in a slurry, which was refluxed for 20 hours, filtered to remove precipitated salts, and stripped of solvent by evaporation of the solvent under reduced pressure. The residue was dissolved in a toluene/diethyl ether mixture, and washed sequentially with 5% HCl, 5% NaOH and 5% $Na_2CO_3$. After the removal of solvent, there remained 349 g of a clear, yellow liquid. The physical properties of this liquid are indicated below in Table V. Samples of this composition had solidified by the end of 1 year's exposure to −24° C. However, other samples of this liquid remain fluid throughout storage at room temperature for a period of two years.

TABLE V

Physical Properties of Composition of Example 9

| | |
|---|---|
| Viscosity | |
| 40° C.: | 66.8 cPs |
| 100° C.: | 7.0 cPs |
| Pour Point: | −19° C. |
| Acid Number: | 0.01 |
| High Pressure AIT: | 270° C. |
| Hydrolytic Stability: | Pass |
| Elastomeric Compatibility (% Volume Change) | |
| Viton I: | +5.2% |
| Viton II: | +3.5% |
| EPR: | +0.3% |

Example 10 exemplifies a sodium salt sequential addition process utilizing only tar acids as the aryloxy reagent.

EXAMPLE 10

Sodium (32.2 g, 1.40 g-atom) was added over a 45 minute period at 20° to 36° C. to 188.14 g of a tar acid mixture of the same composition as used in Example 9 in 940 mL dry THF. The mixture was heated to 67° C. for 3 hours. To 194.0 g (1.94 mole) trifluoroethanol in 1060 mL dry THF was added 40.5 g (1.76 g-atom) sodium in pieces over a 45 minute period, with cooling. The resulting mixture was heated to 67° C. for 5 hours. The sodium tar acid solution was slowly added to a solution of 17.40 g (0.50 mole) $(PNCl_2)_3$ in 1000 mL THF over a 1 hour period at 21° to 31° C. The mixture was heated to 59° C., cooled to 29° C. and the sodium trifluoroethoxide solution added over a 1 hour period. The reaction was allowed to proceed overnight (18 hours) at 67° C. The resultant slurry was filtered, and the filtrate washed with 5% NaOH, 5% HCl, and with 5% $NaHCO_3$, dried over $MgSO_4$, filtered, and solvent and volatiles were removed at 84° C. at 0.05 torr, leaving 303.7 g (76.4% yield) of clear yellow liquid. This liquid was analyzed as having the distribution of phosphazene compounds shown in Table VI, and the properties shown in Table VIII.

TABLE VI

Components of Composition of Example 10

| Component | Distribution (wt %) |
|---|---|
| $P_3N_3(OCH_2CF_3)_6$ | 1.9 |
| $P_3N_3(OCH_2CF_3)_5(OAr)$ | 4.0 |
| $P_3N_3(OCH_2CF_3)_4(OAr)_2$ | 17.7 |
| $P_3N_3(OCH_2CF_3)_3(OAr)_3$ | 66.3 |
| $P_3N_3(OCH_2CF_3)_2(OAr)_4$ | 9.5 |
| $P_3N_3(OCH_2CF_3)(OAr)_5$ | Trace |
| $P_3N_3(OAr)_6$ | 0 |

COMPARATIVE EXAMPLE C11

The procedure of Example 10 was repeated, using 188.14 g (1.54 mole) m-ethylphenol in place of the tar acid mixture. This resulted in 383.3 g (96.3% yield) of a clear amber liquid. This liquid was analyzed as having the components indicated below in Table VII, and the properties indicated in Table VIII. Samples of this composition remained fluid after long standing at −20° C. However, samples of this composition had a High Pressure AIT of 225° C., which does not meet minimum High Pressure AIT Standards of MIL-H-19457C.

TABLE VII

Components of Composition of Example C11

| Component | Distribution (wt %) |
|---|---|
| $P_3N_3(OCH_2CF_3)_6$ | 1.0 |
| $P_3N_3(OCH_2CF_3)_5(OAr)$ | 3.0 |
| $P_3N_3(OCH_2CF_3)_4(OAr)_2$ | 14.4 |
| $P_3N_3(OCH_2CF_3)_3(OAr)_3$ | 68.6 |
| $P_3N_3(OCH_2CF_3)_2(OAr)_4$ | 12.8 |
| $P_3N_3(OCH_2CF_3)(OAr)_5$ | Trace |
| $P_3N_3(OAr)_6$ | 0 |

COMPARATIVE EXAMPLE C12

The procedure of Example 10 was repeated using 188.14 g (1.54 moles) p-ethylphenol in the place of the tar acid mixture. The product was a solid of the average composition: P$_3$N$_3$(OCH$_2$-CF$_3$)$_{3.2}$(OC$_6$H$_4$-p-CH$_2$CH$_3$)$_{2.8}$.

Comparative Example C13 exemplifies preparation of a phenoxy, trifluoroethoxy substituted phosphazene by a PTC bulk procedure.

COMPARATIVE EXAMPLE C13

Two samples were prepared using duplicate runs of the following procedure. A 500 ml flask with magnetic stirrer, thermometer, condenser, gas dispersion tube and addition funnel was charged with 14.1 g (0.15 mole) phenol, 12.0 g (0.15 mole) trifluoroethanol, 19.5 g (0.30 mole) KOH pellets and 120 mL H$_2$O. The flask was purged with N$_2$ for 30 minutes. A 35° C. solution of 17.4 g (0.50 mole) cyclic (PNCl$_2$)$_3$ and 5.8 g (0.018 mole) tetrabutylammonium bromide in 100 mL chlorobenzene was added over a one hour period while the temperature rose from about 30° to about 47° C. The resulting mixture was heated at 70° C. for 28 hours. During the last 6 hours an additional 3.0 g trifluoroethanol, 1.4 g phenol and 3.0 g KOH were added. The product mixture was cooled, the aqueous phase removed, and the organic phase washed successively with 5% aqueous NaOH, 5% aqueous HCl and 5% aqueous NaHCO$_3$, dried over MgSO$_4$, filtered, and the solvent and volatiles removed. The products from the two duplicate runs were liquids nearly identical in physical properties, with an 88% product yield and were identified as having the average composition: P$_3$N$_3$(OCH$_2$CF$_3$)$_3$(OC$_6$H$_5$)$_3$. The physical properties of one of these liquids is indicated below in Table VIII. Both of these liquids partially crystallized on standing at 5° C.

COMPARATIVE EXAMPLE C14

When the PTC sequential preparation of the average composition P$_3$N$_3$(OCH$_2$CF$_3$)$_3$(OC$_6$H$_5$)$_3$ was performed using the same amounts of reagents as in Comparative Example C13, a crystalline product was obtained.

COMPARATIVE EXAMPLE C15

A composition of the average formula P$_3$N$_3$(OCH$_2$CF$_3$)$_{3.25}$(OC$_6$H$_5$)$_{2.75}$ was prepared by aa PTC bulk addition procedure. This composition also partially crystallized at 5° C.

COMPARATIVE EXAMPLE C16

Three samples were also prepared using a sodium salt, sequential addition procedure. One sample, of average composition P$_3$N$_3$(OCH$_2$CF$_3$)$_{2.9}$(OC$_6$H$_5$)$_{3.1}$, was a crystalline solid at room temperature. A second sample, of average composition P$_3$N$_3$(OCH$_2$CF$_2$)$_{4.4}$(OC$_6$H$_5$)$_{1.6}$, partially crystallized on standing at room temperature, and completely crystallized while testing the pour point. The third sample partially crystallized on standing at room temperature, and was analyzed as having the properties indicated below in Table VIII.

COMPARATIVE EXAMPLE C17

Several trimeric phosphazene compositions were prepared from m-methylphenol and trifluoroethanol using a sodium salt, sequential addition procedure. The resulting compositions on the average had trifluoroethoxy/aryloxy ratios of 4.3:1.7, 1:1, and 1.8:4.2. All three compositions solidified upon standing at room temperature. The properties of one of these compositions is indicated below in Table VIII.

Comparative Example C18 exemplifies the preparation of a phosphazene composition according to a PTC sequential addition procedure, with post reaction with an aryloxide.

COMPARATIVE EXAMPLE C18

A solution of 278.4 g (0.80 mole) of (PNCl$_2$)$_3$ and 92.85 g (0.29 mole) Bu$_4$NBr in 900 mL chlorobenzene was charged to a flask fitted with stirrer, thermometer, reflux condenser, nitrogen inlet and 1000 mL addition funnel. A mixture of 125.2 g (1.92 mole) of KOH pellets, 112.4 g (1.04 mole) m-methylphenol, 142.7 g (0.94 mole) m-(trifluoromethyl)phenol and water to make a 1000 mL solution was added to the (PNCl$_2$)$_3$ solution over approximately one hour, at 18° to 29° C. After stirring for an additional hour at 20° to 29° C., the pH of the aqueous phase was 7.5. A mixture of 187.9 g (2.88 mole) of KOH pellets, 288.0 g (2.88 mole) trifluoroethanol and water to make one liter of solution was added over the course of approximately one hour, at 20° to 28° C. The reaction mixture was heated to 40° C. for 1.5 hours, allowed to stand at room temperature overnight and the phases separated. The organic phase was dried with MgSO$_4$ and filtered. A 10 mL portion of the filtrate was removed. The remainder of the filtrate was postreacted with 0.40 mole of sodium-m-(trifluoromethyl)-phenoxide for one hour at 60° C. The product mixture was washed with 5% aqueous HCl and 5% aqueous NaHCO$_3$, dried with MgSO$_4$, and filtered. The crude product of this procedure was 597.1 g (97.6% yield) of yellow liquid. A 523.4 g portion of the crude product was distilled, collecting a 23.84 g forecut and a 430.0 g (82.2%) main fraction plus 62.5 g of residue. The main fraction contained less than 0.05% residual chlorine. It was dissolved in toluene/ether and passed thru a column of ion exchange resin. The solvent was removed and the acid number found to be 0.13. The product was redissolved in 1/1 toulene/ether and washed with 5% aqueous NaCO$_3$, dried over MgSO$_4$ and filtered. Solvent and volatiles were removed, leaving a pale yellow liquid with an acid number of 0.04 mg KOH/g of fluid. A 369.2 g portion of this material was redistilled, collecting a 332.9 g main fraction of clear, colorless liquid. The physical properties of this liquid are indicated below in Table VIII. Samples of this composition remained fluid after prolonged standing at $-20°$ C. However, this composition had a flash point of 271° C., which is below the minimum standard for MIL-H-19457C.

COMPARATIVE EXAMPLE C19

A composition was prepared by a PTC sequential addition procedure, utilizing phenol, m-methylphenol and trifluoroethanol. This procedure resulted in a phosphazene based composition of the average composition: P$_3$N$_3$(OCH$_2$CF$_3$)$_{3.4}$(OC$_6$H$_5$)$_{1.3}$(OC$_6$H$_4$-m-CH$_3$)$_{1.3}$. The crude product obtained was divided into two portions, which were purified using different procedures.

In the one procedure, the crude product was rewashed sequentially with 5% aqueous HCl, 5% NaOH and 5% aqueous NaHCO$_3$. After drying with MgSO$_4$, filtering and removing solvent, there remained 333.7 g yellow liquid product having 0.13% total chloride and an acid number of 4.28. A 295.6 g portion of the liquid was distilled, collecting a forecut of 13.7 g, a main fraction of 252.1 g of nearly colorless liquid, and 29.8 g of residue. The main fraction had 0.11% Cl and an acid number of 0.20. It was dissolved in equal volumes of diethylether/toluene, washed with 5% aqueous $Na_2CO_3$ dried with $MgSO_4$, filtered and freed of solvents, leaving 237.5 g of liquid having an acid number of 0.08. This liquid was redistilled, collecting a first fraction of 12.22 g, a main fraction of 200.17 g and a third fraction of 8.99 g, leaving 2.58 g of residue. The main fraction had an acid number of 0.02. On standing, this composition partially crystallized at room temperature.

In the other purification procedure, the other half of the crude liquid product was passed through a column of an ion exchange resin to remove residual $Bu_4NBr$. The liquid was filtered and the solvents removed, leaving 327.2 g of straw colored liquid containing 0.20% residual chloride and having an acid number of 2.62. A 293.87 g portion of this material was distilled, collecting a 6.36 g forecut, a 238.35 g main fraction, and 25.5 g third fraction, leaving 21.63 g of residue. The main and third fractions contained some tributyl amine. They were combined and subjected to 0.05 torr on a rotary evaporator at 80° C. for 2 hours, thereby removing approximately 35% of the remaining tributyl amine. The product was dissolved in 1/1 toluene/ether, washed with 5% aqueous HCl, and 5% aqueous $Na_2CO_3$, dried over $MgSO_4$, filtered and the solvents removed, leaving 258.7 g of pale yellow liquid having an acid number of 0.24. A 247.6 g portion of this material was redistilled, collecting a forecut of 10.04 g and a main fraction of 225.82 g leaving a 10.47 g residue. The main fraction was a clear colorless liquid. Its properties are indicated below in Table VIII. It also crystallized on standing at −20° C.

COMPARATIVE EXAMPLES C20, C21, C25;

Examples 22-24

Several phosphazene based fluid compositions were synthesized. The compositions of Examples 22, 23 and 24 are various embodiments of the present invention. The phosphazene based compositions of Comparative Examples C20, C21 and C25 do not embody the present invention, but are provided as a basis for comparison. The average composition of the fluids for Examples 22-24 and Comparative Examples C20, C21 and C25, as well as these fluids' physical characteristics and their method of preparation, are indicated below in Table IX.

All of the compositions of Examples 22-24 and Comparative Examples C20, C21 and C25 were liquid at −20° C.

These examples have been presented only to demonstrate operability and to provide a basis for comparing certain embodiments of the present invention with compositions not included within the scope of the invention. The scope of the present invention, however, is not limited to the specific embodiments presented above, but includes equivalent embodiments and modifications as defined by the following claims:

TABLE VIII $P_3N_3(OCH_2CF_3)_a(OC_6H_4X)_b(OC_6H_4Y)_c$

| | Example No. | | | | | | | |
|---|---|---|---|---|---|---|---|---|
| Synthesis Procedure | 10 Na, sequential | C11 Na, sequential | C12 Na, sequential | C13 PTC, bulk | C16 Na, sequential | C17 Na, sequential | C18 PTC, sequential | C19 PTC, sequential |
| Substituent X | R, mixed | m-$CH_2CH_3$ | p-$CH_2CH_3$ | H | H | m-$CH_3$ | m-$CH_3$ | H |
| Substituent Y | N/A | N/A | N/A | N/A | N/A | N/A | m-$CF_3$ | m-$CH_3$ |
| Average Composition | | | | | | | | |
| Values a | 3.2 | 3.2 | 3.2 | 3 | 1.9 | 3 | 3.5 | 3.4 |
| b | 2.8 | 2.8 | 2.8 | 3 | 4.1 | 3 | 1.4 | 1.3 |
| c | 0 | 0 | 0 | 0 | 0 | 0 | 1.1 | 1.3 |
| Viscosity, | | | | | | | | |
| 40° C. | 68.5 | 43.9 | SOLID | 119.9 | 94.4 | 58.2 | 37.0 | 38.3 |
| 100° C. | 5.81 | 5.2 | | 8.7 | 7.5 | 5.4 | 4.3 | 4.4 |
| Pour Point °C. | −20 | −25.5 | | | −8 | −19 | −27 | −24 |
| Acid No. | | 0.04 | | | | | 0.02 | 0.11 |

TABLE IX $P_3N_3(OCH_2CF_3)_a(OC_6H_4X)_b(OC_6H_4Y)_c$

| | Example No. | | | | | |
|---|---|---|---|---|---|---|
| Synthesis Procedure | C20 PTC, sequential | C21 Na salt, sequential | 22 Na salt, sequential | 23 PTC, sequential | 24 PTC, bulk | C25 PTC, bulk |
| Substituent X | m-$CF_3$ | H | H | H | H | H |
| Substituent Y | N/A | P-$CH_2CH_3$ | m-,p-$CH_2CH_3$ | m-,p-$CH_2CH_3$ | m-,p-$CH_3$ | p-Cl |
| Average Composition | | | | | | |
| Values a | 3 | 3 | 3.10 | 3.14 | 3.4 | 3.4 |
| b | 3 | 2 | 1.93 | 1.91 | 1.3 | 1.6 |
| c | 0 | 1 | 0.97 | 0.95 | 1.3 | 1 |
| Viscosity, | | | | | | |
| 40° C. | 41.84 | 59.78 | 48.99 | 53.45 | 40.3 | 40.6 |
| 100° C. | 5.20 | 6.17 | 5.57 | 5.58 | 4.6 | 4.8 |
| Pour Point °C. | −23 | −11 | −12 | −15 | −15 | −15 |
| Acid No. | 0.84 | 0.06 | 0.01 | 0.63 | 0.62 | 0.85 |
| Elastomer Compatability % Volume Swell | | | | | | |
| Viton I | +11.6 | +4.6 | +5.2 | +2.8 | +3.97 | +11.0 |
| Viton II | +9.4 | +1.4 | +3.5 | +3.9 | | |
| EPR | −4.1 | −0.4 | +0.3 | −1.9 | | +3.55 |

TABLE IX-continued

| | $P_3N_3(OCH_2CF_3)_a(OC_6H_4X)_b(OC_6H_4Y)_c$ | | | | | |
|---|---|---|---|---|---|---|
| | Example No. | | | | | |
| Synthesis Procedure | C20 PTC, sequential | C21 Na salt, sequential | 22 Na salt, sequential | 23 PTC, sequential | 24 PTC, bulk | C25 PTC, bulk |
| Flash Point °C. | 313 | 293 | 293 | 302 | 299 | 285 |
| High Pressure AIT °C. | 332 | 254 | 267 | 270 | 276 | 290 |

We claim:

1. A functional fluid composition comprising a plurality of different cyclic phosphazene compounds of the general formula:

$$(P=N)_n(R)_a(R')_b(R'')_c(R''')_d$$

wherein;
R is at least one alkoxy moiety described by the general formula —$OCH_2(CF_2)_yX$, with X being hydrogen or fluorine and y being equal to 1 to about 10;
R', R" and R''' are different aryloxy moieties, each of R', R" and R''' being selected from the group consisting of phenoxy, alkoxy phenoxys, alkylphenoxys, chlorinated phenoxys, fluorinated phenoxys, arylphenoxys, phenoxy phenoxys, fluoroalkyl phenoxys, fluoroalkoxy phenoxys, chlorinated phenoxy phenoxys, fluorinated phenoxys phenoxys and mixtures thereof;
n is equal to 3 to about 4;
for each of said phosphazene compounds, each of a, b, c, and d is equal to or greater than zero such that the sum a+b+c+d is equal to 2n; and
for the composition as a whole, the average value of each of a, b, c, and d is greater than 0; and
wherein each of said different phosphazene compounds is present in an amount less than 70% by weight of the total phosphazene content of said composition.

2. The functional fluid composition of claim 1 wherein the ratio of the average value of a, for the composition as a whole, to the sum of the average values of b, c and d, for the composition as a whole, is about 0.5:1 to about 8:1.

3. The functional fluid composition of claim 2 wherein the ratio is about 0.8:1 to about 5:1.

4. The functional fluid composition of claim 3 wherein the ratio is about 1.3:1 to about 1.9:1.

5. The functional fluid composition of claim 1 wherein said composition includes at least three of said different phosphazene compounds, each of said different phosphazene compounds being present in an amount less than 50% by weight of the total phosphazene content of said composition.

6. The functional fluid composition of claim 5 wherein at least two of said different phosphazene compounds are each present in an amount less than 35% by weight of the total phosphazene content of said composition.

7. The functional fluid composition of claim 1 wherein at least 90% by weight of the alkoxy moieties present in all of said phosphazene compounds combined are trifluoroethoxy.

8. The functional fluid composition of claim 1 wherein at least 80% by weight of the aryloxy moieties present in all of said phosphazene compounds combined are selected from the group consisting of phenoxy, alkyl phenoxys, and alkoxy phenoxys.

9. The functional fluid composition of claim 8 wherein at least 90% by weight of the aryloxy moieties are selected from the group consisting of phenoxy, methylphenoxys, ethylphenoxys, dimethylphenoxys and mixtures thereof.

10. The functional fluid composition of claim 9 wherein at least 80% by weight of said aryloxy moieties are selected from the group consisting of phenoxy, m-methylphenoxy and p-methylphenoxy.

11. The functional fluid composition of claim 10 wherein at least 90% by weight of said aryloxy moieties are selected from the group consisting of phenoxy, m-methylphenoxy and p-methylphenoxy.

12. The product of the process comprising reacting a cyclic dichlorophosphazene compound, having 3 to about 4 phosphazene units, with (a) at least one alkanol reactant generally described by the formula $HOCH_2(CF_2)_yX$, with X being hydrogen or fluorine and y being equal to 1 to about 10, and (b) at least three different phenolic reactants selected from the group consisting of phenol, alkoxy phenols, alkyl phenols, chlorinated phenols, fluorinated phenols, aryl phenols, phenoxy phenols, fluoroalkyl phenols, fluoroalkoxy phenols, chlorinated phenoxy phenols, fluorinated phenoxy phenols and mixtures thereof said reaction occurring in a medium comprising a mixture of water, a base, a water-immiscible solvent and a phase-transfer catalyst.

13. The product of claim 12 wherein the phase transfer catalyst is an alkyl, aryl or aralkyl ammonium or phosphonium salt.

14. The product of claim 13 wherein the phase transfer catalyst is one having the structure:

$$(R^{iv})_4AX$$

wherein the $(R^{iv})$'s are the same or different alkyl, aryl or aralkyl group, A is nitrogen or phosphorus, and X is halogen, OH, $HSO_4$, $NO_3$, $BH_4$, $IO_4$, $ClO_4$, CN, $N_3$, $OCH_3$, tosylate or benzoate.

15. The product of claim 14 wherein the $(R^{iv})$'s are the same or different alkyl group, and X is chlorine or bromine.

16. The product of claim 15 wherein the molar ratio of said alkanol reactant and said phenolic reactants to said dichlorophosphazene units is about 2:1 to about 2.5:1.

17. The product of claim 16 wherein the molar ratio of said alkanol reactant to said phenolic reactants is about 5:1 to about 0.8:1.

18. The product of claim 16 wherein about 40% to about 60% by weight of said phenolic reactants is phenol.

* * * * *